(12) United States Patent
Bakker et al.

(10) Patent No.: US 7,247,489 B2
(45) Date of Patent: Jul. 24, 2007

(54) ION-DETECTING MICROSPHERES AND METHODS OF USE THEREOF

(75) Inventors: Eric Bakker, Auburn, AL (US); Martin Telting-Diaz, Brooklyn, NY (US); Mike Bell, Fullerton, CA (US)

(73) Assignees: Auburn University, Auburn, AL (US); Beckman Coulter, Inc., Fullerton, CA (US)

( * ) Notice: Subject to any disclaimer, the term of this patent is extended or adjusted under 35 U.S.C. 154(b) by 273 days.

(21) Appl. No.: 10/384,082

(22) Filed: Mar. 7, 2003

(65) Prior Publication Data

US 2004/0058384 A1 Mar. 25, 2004

Related U.S. Application Data

(60) Provisional application No. 60/363,180, filed on Mar. 11, 2002.

(51) Int. Cl.
*G01N 33/20* (2006.01)
*G01N 33/52* (2006.01)

(52) U.S. Cl. .................. 436/74; 422/82.05; 422/82.06; 422/82.07; 422/82.08; 422/82.09; 422/82.11; 436/73; 436/79; 436/80; 436/81; 436/82; 436/83; 436/84; 436/169; 436/172; 436/523; 436/528; 436/531; 526/318; 526/318.4; 526/319; 526/330

(58) Field of Classification Search .................. 422/56, 422/82.01–82.03, 82.05–82.09, 82.11; 436/73–74, 436/76–77, 79–84, 149–151, 169, 172, 523, 436/528, 531, 543; 205/781.5; 526/318–319, 526/321, 330, 344, 344.3
See application file for complete search history.

(56) References Cited

U.S. PATENT DOCUMENTS

| | | | |
|---|---|---|---|
| 4,463,032 A * | 7/1984 | Arndt et al. | 427/222 |
| 4,507,425 A * | 3/1985 | Weaver | 524/460 |
| 5,198,301 A * | 3/1993 | Hager et al. | 428/355 AK |
| 5,238,548 A * | 8/1993 | van der Wal et al. | 204/418 |
| 5,260,195 A * | 11/1993 | Azhar et al. | 435/25 |
| 5,567,627 A * | 10/1996 | Lehnen | 436/518 |
| 5,585,241 A * | 12/1996 | Lindmo | 435/6 |
| 5,644,069 A * | 7/1997 | Liu et al. | 73/23.2 |
| 5,747,349 A * | 5/1998 | van den Engh et al. | 436/172 |
| 6,143,570 A * | 11/2000 | Alder et al. | 436/74 |
| 6,190,612 B1 * | 2/2001 | Berger et al. | 422/82.07 |
| 6,254,831 B1 * | 7/2001 | Barnard et al. | 422/82.08 |
| 6,277,330 B1 * | 8/2001 | Liu et al. | 422/82.05 |
| 6,548,310 B1 * | 4/2003 | Murata et al. | 436/518 |
| 6,908,770 B1 * | 6/2005 | McDevitt et al. | 436/518 |

FOREIGN PATENT DOCUMENTS

| | | | |
|---|---|---|---|
| WO | 97/39337 | * | 10/1997 |
| WO | 00/54039 | * | 9/2000 |

OTHER PUBLICATIONS

Pretsch, E. et al, Helvetica Chimica Acta 1980, 63, 191-196.*
Harker, R. Chemistry in New Zealand 1990, 54, 59-60.*
Daunert, S. et al, Analytical Chemistry 1990, 62, 1428-1431.*
Bochenska, M. et al, Journal of Inclusion Phenomena and Molecular Recognition in Chemistry 1991, 10, 19-27.*
Xu, W. et al, Chinese Chemical Letters 1993, 4, 179-180.*
Xie, Z. et al, Journal of the American Chemical Society 1994, 116, 1907-1913.*
Cross, G. G. et al, Talanta 1994, 41, 1589-1596.*
King, B. T. et al, Journal of the American Chemical Society 1996, 118, 3313-3314.*
Xie, Z. et al, Inorganic Chemistry 1998, 37, 6444-6451.*
Smirnova, A. L. et al, Electroanalysis 1999, 11, 763-769.*
Heng, L. Y. et al, Analytical Chemistry 2000, 72, 42-51.*
Heng, L. Y. et al, Analytica Chimica Acta 2000, 403, 77-89.*
Heng, L. Y. et al, Electroanalysis 2000, 12, 178-186.*
Heng, L. Y. et al, Electroanalysis 2000, 12, 187-193.*
Malinowska, E. et al, Analytica Chimica Acta 2000, 421, 93-101.*
Tsang, C.-W. et al, Inorganic Chemistry 2000, 39, 3582-3589.*

(Continued)

*Primary Examiner*—Arlen Soderquist
(74) *Attorney, Agent, or Firm*—Hogan & Hartson LLP

(57) ABSTRACT

This invention provides methods of using ion-detecting microspheres containing an ionphore and a chromoionphore in clinical laboratory instrumentation such as flow cytometry for sample analysis. In one embodiment, the microspheres are contacted with a flowing stream of a sample under conditions that allow the ion-selective ionophores to complex with the ions in the sample, and to cause deprotonation of the chromoionophore. The complexes are then exposed to an excitation wavelength light source suitable for exciting the deprotonated chromoionophore to emit a fluorescence signal pattern. Detection of the fluorescence signal pattern emitted by the deprotonated chromoionophore in microspheres containing the complexes allows for determination of the presence of the target ions in the sample. In one embodiment, lead ion-detecting microspheres are provided that can detect nanomolar levels of lead ions with response times on the order of minutes.

24 Claims, 8 Drawing Sheets

OTHER PUBLICATIONS

Telting-Diaz, M. et al, Analytical Chemistry 2001, 73, 5582-5589.*
Peper, S. et al, Analytical Chemistry 2002, 74, 1327-1332.*
Qin, Y. et al, Analytical Chemistry 2003, 75, 3038-3045.*
Qin, Y. et al, Analytical Chemistry 2003, 75, 6002-6010.*
Lerchi, M. et al, Analytical Chemistry 1992, 64, 1534-1540.*
Lerchi, M. et al, Analytical Chemistry 1994, 66, 1713-1717.*
Shortreed, M. et al, Analytical Chemistry 1996, 68, 2656-2662.*
Huang, M.-C. et al, SPIE 1998, 3256, 178-185.*
Kurihara, K. et al, Analytical Chemistry 1999, 71, 3558-3566.*
Tsagkatakis, I. et al, Analytical Chemistry 2001, 73 315-320.*
Goodey, A. et al, Joural of the American Chemical Society 2001, 123, 2559-2570.*
Hisamoto, H. et al, Sensors and Actuators B 1995, 29, 378-385.*
Esson, J. M. et al, Analytica Chimica Acta 2000, 404, 83-94.*

* cited by examiner

ION-DETECTING MICROSPHERES AND METHODS OF USE THEREOF

CROSS-REFERENCE TO RELATED APPLICATIONS

The present invention claims priority to Provisional Application No. 60/363,180, filed on Mar. 11, 2002, entitled "Rapid Trace Level Sensing Fluorescent Microspheres."

GOVERNMENT INTERESTS

The invention was made in the course of work supported by grant No. GM59716 from the National Institutes of Health. The United States government has certain rights in this invention.

BACKGROUND OF THE INVENTION

1. Field of the Invention

The present invention is related to systems for detecting target ions in a sample, and more specifically, to ion-detecting microspheres and methods of use thereof in clinical laboratory instrumentation such as flow cytometry for sample analysis.

2. Description of the Prior Art

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

The analysis of complex biological fluids, such as whole blood, serum, and urine, is of paramount importance in clinical chemistry. Electrolytes such as sodium ions and potassium ions are routinely assessed using carrier-based ion-selective electrodes (ISEs) (1–2). With more than one billion ISE measurements being performed annually world wide in clinical laboratories, this class of chemical sensors plays a crucial role in laboratory diagnostics. Trends in analytical chemistry continue to move toward the development of miniaturized systems, and there is a great interest in streamlining all available assays into one common method. One approach towards achieving this goal is the use of optical readout methodologies.

Several approaches have been developed for ion analyses that use fluorescence transduction (3–17). This is primarily due to the high signal-to-noise ratio afforded by this detection method, making it an attractive choice for creating sensors of reduced size. Most ion-selective optical sensors use the same carriers previously developed for use in ISEs, and they obey bulk extraction principles consistent with traditional optode theory (2).

Typically, an optode membrane is composed of a plasticized poly-(vinyl chloride) (PVC) matrix, an ionophore that selectively binds the primary ion, ionic sites that facilitate mass transfer of ions from the aqueous sample to a hydrophobic sensing phase, and a hydrogen ion-selective fluorescent chromoionophore (fluoroionophore), which is responsible for signal transduction. Other approaches for ion determinations utilized particle-based technologies. Lubbers et al. have reported optical nanoprobes for measuring the pH and $pO_2$ of physiological structures (10). More recently, Kopelman et al. reported both acryl amide and PVC-type nanometer-sized sensing spheres that have proven to be quite useful in interrogating intracellular environments (3, 4, 5, 19). Bakker and group have prepared micrometer-sized particles by various methods, including heterogeneous polymerization (13), solvent casting (17), and very recently, with the use of a sonic stream particle casting apparatus (16). Spatial and spectral characterization of the particles was performed by fluorescence microscopy/spectroscopy. However, the use of this technique has not been described for high throughput screening applications prior to the present invention.

In an attempt to increase the throughput of ion determinations, Kim et al. have described a 96-well plate-format absorbance-based optode that requires micro volume samples and that could be read using existing clinical laboratory instrumentation (20). An even more promising technique, however, that offers rapid, high-throughput analyses with multiplexing capabilities is flow cytometry. Microspheres have been used for flow cytometric applications for more than 25 years (21), and they are commonly used for multiplexed analyses. It has been demonstrated that as many as 64 different analytes can be screened simultaneously using microsphere-based technologies (20–24). With large surface area available for attaching numerous molecular recognition chemistries (6) and a core that can be impregnated with encoding dyes (25), microspheres have played an important role in the development of suspension array technologies (26). Numerous biologically relevant analytes have been detected using microsphere-based cytometry (7, 8, 11, 12, 24, 27–29). Electrolytes, however, are a class of analytes that have never been assessed with this technique.

Lower detection limits, smaller sample volumes, faster response times and high selectivity are among the many requirements that must be met in the trace level analysis of complex samples. Towards this end, optode films based on neutral ionophores have proven to be a highly promising technology for the analysis of heavy metal ions. Over the past decade, an increasing number of cation-exchange based systems including those for $Pb^{2+}$, $Cu^{2+}$, $Hg^{2+}$, $Ag^+$, $UO_2^{2+}$, have been reported (30–34).

For the analysis of lead ions, optode systems that incorporate highly selective ionophores have been used. Those that may contain sulfur coordinating functionalities, like a calixarene bearing a —SH pending group or a di-thioamide derivative, have demonstrated increased success in polymer membranes of ISEs where they have been shown to exhibit detection limits that extend even to picomolar levels with electrodes that are carefully tailored (35, 36). In optode systems, selective ionophores incorporated with a lipophilic chromoionophore and required anionic sites have been examined with view to their use in environmental monitoring (30). As for all conventional cation-exchange based systems, lead optodes follow predicted theory as given by the associated equilibrium of transfer of the lead analyte species and hydrogen ions into the plasticized PVC optode phase. In particular, the lead complexing agent 3,6-dioxaoctanedithioamide derivative, that is, ETH 5435, in conjunction with the absorption changing properties of chromoionophore ETH 5418, was found to exhibit excellent selectivity against all relevant alkaline and alkaline-earth metal ions, thus allowing lead measurable concentrations to extend to the sub-nanomolar range.

Antico et al. (37) have reported on optode films incorporating the ionophore ETH 5493, which is a mono-thio oxodiamide derivative of ETH 5435. While the use of such an ionophore offers less good selectivity with respect to the alkaline-earth metal ions $Ca^{2+}$ and $Mg^{2+}$ than the di-thioamide ligand, no irreversible sensing film poisoning upon exposure to $Ag^+$ or $Hg^+$ ions does occur.

These papers on ionophore-based optodes have shown that the selectivity and detection limits are sufficient to reach sub-nanomolar detection limits. However, a significant drawback is the high sensing volume of the optode film, which requires typically on the order of 10 µmoles of ions to be extracted from the sample in order to achieve the desired optical response. Consequently, massive volumes of sample (many liters) and very long response times (many hours) in a continuous flowing system have so far been required to accurately measure low levels of heavy metals in aqueous samples. A drastic miniaturization of the sensing element should be able to alleviate this important problem.

SUMMARY OF THE INVENTION

Accordingly, this invention provides ion-detecting microspheres for detecting target ions in a sample, and to methods of use thereof in clinical laboratory instrumentation such as flow cytometry for sample analysis. This invention is based on the discovery that ion-detecting microspheres can be used in conjunction with existing clinical laboratory instrumentation such as flow cytometry as a diagnostic tool for rapid, high-throughput analysis of a sample. The ion-detecting microspheres of this invention were shown to possess acceptable sensitivity, selectivity, and precision for the potential clinical determination of ions. This invention further demonstrates that multiplexed measurements of two or more types of ions in a sample are possible using this analytical method.

More specifically, one aspect of this invention provides a method of detecting target ions in a sample, comprising:

(a) providing polymeric ion-detecting microspheres, said microspheres comprising an ionophore selective for said target ions and a chromoionophore;

(b) contacting said microspheres with a flowing stream of said sample under conditions that allow the ion-selective ionophores to bind and form complexes with the ions, if present in the sample, and to cause deprotonation of the chromoionophore;

(c) exposing the deprotonated chromoionophore, if formed, to an excitation wavelength light source suitable for exciting the deprotonated chromoionophore to emit a fluorescence signal pattern; and (d) detecting the fluorescence signal pattern emitted by the complexes, if present, by a detection means for detecting the fluorescence signal pattern, wherein said fluorescence signal pattern is inversely proportional to the amount of said target ions in said sample.

In one embodiment, the ion-detecting microspheres are immobilized on a substrate prior to the contacting step.

This invention further provides rapidly responsive ion-detecting polymeric microparticles for detecting metal ions in a sample. In one embodiment, the ion-detecting microspheres comprise a lipophilic ionophore selective for the metal ions, a chromoionophore selective for hydrogen ions, and a fluorescent dye, wherein said chromoionophore becomes deprotonated when metal ions are present in said sample, and wherein the deprotonated form of the chromoionophore is absorbent at the frequency of the fluorescence emission of the dye.

In particular, lead ion-detecting microspheres are provided that respond with a high degree of sensitivity (i.e., can detect nanomolar levels of lead ions) and display extremely enhanced equilibrium response times (i.e., on the order of minutes). In addition, the lead ion-detecting microspheres only require sample volumes on the order of milliliters, and demonstrate high response stability for various lead ion concentration changes.

This invention further provides a method of detecting nanomolar or sub-nanomolar levels of lead ions in a sample, comprising:

(a) providing polymeric microspheres comprising an ionophore selective for lead ions, a reference dye, and a chromoionophore selective for hydrogen ions, and a fluorescent dye, wherein the chromoionophore is a chromoionophore that becomes deprotonated when lead ions are present in the sample, and wherein said deprotonated form of said chromoionophore is absorbent at the frequency of the fluorescence emission of said dye (b) contacting said microspheres with a flowing stream of said sample under conditions that allow the ion-selective ionophore to bind and form complexes with the lead ions, if present in the sample, and to cause deprotonation of said chromoionophore;

(c) exposing the complexes, if formed, to an excitation wavelength light source suitable for exciting the fluorescent microspheres of the complexes to emit a fluorescence signal pattern; and (d) detecting the fluorescence signal pattern emitted by the complexes, if present, by a detection means for detecting the fluorescence signal pattern, wherein said fluorescence signal pattern is inversely proportional to the amount of lead ions in the sample.

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail, in which.

DETAILED DESCRIPTION OF THE INVENTION

Figure 1:
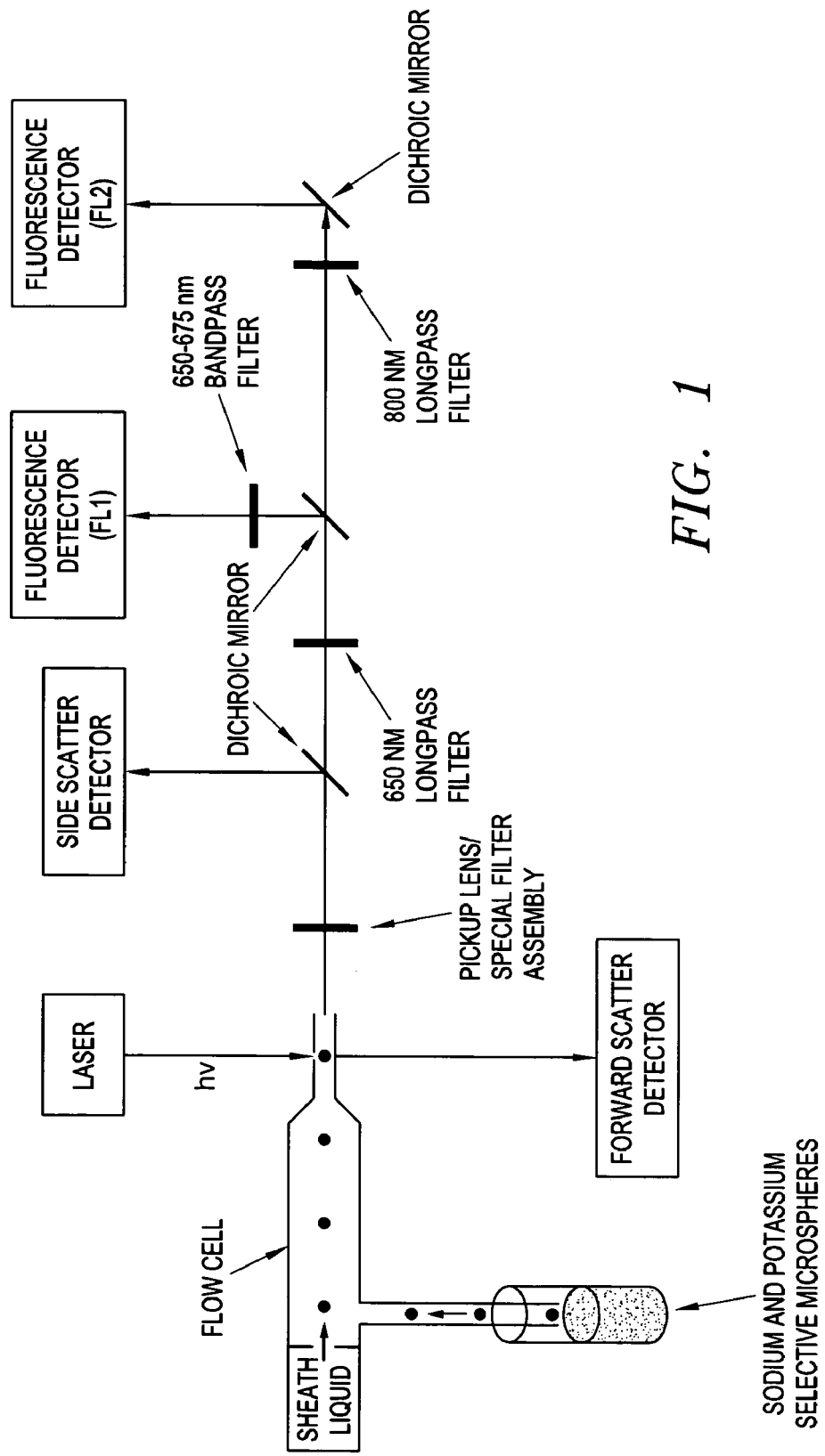
FIG. 1 is a schematic showing the optical configuration of a flow cytometer according to one embodiment of this invention.

This invention provides ion-detecting microspheres for detecting target ions in a sample, and to methods of use thereof in clinical laboratory instrumentation such as flow cytometry for sample analysis. This invention is based on the discovery that ion-detecting microspheres can be used in conjunction with existing clinical laboratory instrumentation such as flow cytometry as a diagnostic tool for rapid, high-throughput analysis of a sample. More specifically, one aspect of this invention provides a method of detecting target ions in a sample, comprising:

(a) providing polymeric ion-detecting microspheres, said microspheres comprising an ionophore selective for said target ions and a fluorescent chromoionophore;

(b) contacting said microspheres with a flowing stream of said sample under conditions that allow the ion-selective ionophores to bind and form complexes with the ions, if present in the sample, and to cause deprotonation of the chromoionophore;

(c) exposing the deprotonated chromoionophore, if formed, to an excitation wavelength light source suitable for exciting the deprotonated chromoionophore of the complexes to emit a fluorescence signal pattern; and (d) detecting the fluorescence signal pattern emitted by the complexes, if present, by a detection means for detecting the fluorescence signal pattern, wherein said fluorescence signal pattern is inversely proportional to the amount of said target ions in said sample.

The term "microsphere" or "microparticle" refers to a micrometer-sized particle which is comprised of a polymeric material which may include, but is not limited to, a thermoplastic (e.g., one or more of polystyrenes, polyvinyl chloride, polyacrylate, nylon, substituted styrenes, polyamides, polycarbonate, polymethylacrylic acids, polyaldehydes, and the like), latex, or acrylic. In one embodiment, the microsphere is substantially spherical in shape.

In a preferred embodiment, the polymeric microspheres comprise a monodisperse population having an average particle size (as measured by diameter) in the range of approximately 1 µm to about 20 µm.

Preferably, the microspheres are formed by a sonic stream particle casting apparatus. Briefly, sonic stream particle casting is a method in which two liquids coexisting as two separate phases are brought in contact by flowing from separate storage reservoirs (38). One of the liquids, that is, the polymer solution mixture containing the chemical sensing components (see below), is dissolved in an adequate organic solvent that acts as the core stream. This solution and a second flowing aqueous solution, the so-called sheath liquid, are directed to a chamber where the constant oscillation frequency from a piezoelectric crystal, driven by a frequency generator (e.g., a BK Precision Model 4011, Placentia, Calif.) controls the formation of polymer droplets at a high rate. As the core polymer liquid flows under precisely defined conditions into an injection tube in the chamber and emerges as a liquid jet from a ceramic orifice tip (43 µm diameter), the polymer droplets form within the second moving aqueous stream which flows around the injection tube and emerging jet. Thus, the polymer droplet solvent slowly partitions into the aqueous sheath stream leaving behind small and highly uniform spherical particles that can be collected in a recipient solution for subsequent precipitation and separation, or can be collected directly into small vials for immediate immobilization and analysis. The casting process produces uniform polymeric microspheres of average diameter-ranging between 3 and 30 µm.

Alternatively, the microparticles can be prepared by other methods known to those skilled in the art, such as by a solvent casting method or by heterogeneous polymerization.

In one embodiment, uniform, monodisperse ion-detecting microspheres were prepared from plasticized PVC using a high-throughput particle casting technique. Plasticized PVC was selected as the polymer matrix because it provides a lipophilic environment conducive for retention of active sensing components, and it is known to be a suitable material for ionophore-based sensing (1).

Alternatively, the microspheres comprise a copolymer of methacrylate monomers with different pendant alkyl groups R$_1$ and R$_2$, wherein R$_1$ may be any of C$_{1-3}$ alkyl group, and R$_2$ may be any of C$_{4-12}$ alkyl group, as described in U.S. patent application Ser. No. 10/313,090, the content of which is specifically incorporated in its entirety herein by reference. In accordance with embodiments of the present invention, a copolymer of the present invention has a glass transitional temperature (T$_g$) of about or less than 0° C.

The polymeric microspheres further comprise an ionophore having high selectivity for the target ion. The microspheres may be used in connection with a wide variety of ionophores for detecting different target ions. Examples of such ionophores include, but not are limited to, ionophores selective for target ions such as hydrogen, Li$^+$, Na$^+$, K$^+$, Ca$^{2+}$, or Mg$^{2+}$, metal ions such as Pb$^{2+}$, Cu$^{2+}$, Hg$^{2+}$, Ag$^+$, and oxides such as UO$_2^{2+}$. Examples of ionophores suitable for purposes of this invention include, but are not limited to, potassium ionophore III (BME-44), sodium ionophore X, and lead ionophore ETH 5493. Ionophores of the type described herein above are well known in the art are commercially available or may be prepared using conventional synthetic techniques.

The polymeric microspheres also comprise a chromoionophore to allow for quantitation and/or detection of target ions in the sample, for example as described below with respect to flow cytometric methods. In one embodiment, the chromoionophore is a neutral hydrogen-ion-selective fluorescent chromoionophore (i.e., a fluoroionophore), which is responsible for signal transduction. Deprotonation of the chromoionophore occurs when protons are exchanged by target ions entering the polymeric matrix, and changes in chromoionophore protonation result in measurable changes in its optical behavior.

The ion-detecting sensors of the present invention may also include other additives such as ion-exchangers to enhance the extraction of the target ion from the aqueous sample and the migration of the target ion into the polymer matrix. While any ion exchangers that provide lipophilic anionic sites on the polymer matrix may be used, preferably, carba-closo-dodecaborates, particularly halogenated carborane anions, are used as ion exchangers. Examples of halogenated dodecacarborane cation exchangers suitable for purposes of this invention include, but are not limited to, trimethylammonium-2, 3, 4, 5, 6, 7, 8, 9, 10, 11, 12 undecabromocarborane (TMAUBC) (U.S. patent application Ser. No. 10/313,090), and salts (e.g., trimethylammonium salts) of undecachlorinatedcarborane (UCC), hexabrominatedcarborane (HBC) and undecaiodinatedcarborane (UIC) anions.

It is a discovery of the present invention that ion-detecting microspheres possess acceptable sensitivity, selectivity, and precision for the determination of ions in a sample using existing clinical laboratory instrumentation such as flow cytometry. For example, it was discovered that ion-detecting microspheres such as those described herein can be used in combination with flow cytometry as a useful analytical detection platform for rapid, high-throughput analysis of sample ion concentrations.

FIG. 1 shows one example of a flow cytometry optical system used according to this invention. According to FIG. 1, the microspheres are contacted with a flowing stream of a sample under conditions that allow the ion-selective ionophores to bind the ions, if present in the sample, and thus form a complex with the ions. As the ions form complexes with the ionophore, the chromoionophore in the microsphere becomes deprotonated. The microspheres are then exposed to an excitation wavelength light source suitable for exciting the deprotonated chromoionophore to emit a fluorescence signal pattern. Detection of the fluorescence signal pattern emitted by the deprotonated chromoionophore by a suitable detection means allows for determination of the presence of the target ions in the sample as described below. The detection means can include, but is not limited to, a photodetector, a fluorimeter, a fluorescence microscope, a filter, a charge couple device camera, or a photomultiplier tube.

In one embodiment, the ion-detecting microspheres are immobilized on a substrate prior to the contacting step. Examples of substrates include, but are not limited to, glass, silica, ceramic, nitrocellulose, nylon or other polymeric membrane materials. The substrate may be fabricated in a form of plates including multiple well microplates, sheets, films, slides, gels, membranes, beads, particles, foams, filaments, threads, and like structures. Methods of immobilizing the microspheres onto a substrate may be performed as described herein or by methods known to those skilled in the art.

According to one embodiment of this invention, a method is provided detecting target ions in a sample, wherein the method includes contacting microspheres comprising an ionophore selective for the target ions with a flowing stream of a sample under conditions that allow the ion-selective ionophores to bind and form complexes with the ions, if present in the sample, and to cause deprotonation of the chromoionophore. The contacting conditions are those which allow the ion-selective ionophores and target ions may become bound to each other according to an ion exchange process consistent with classical optode theory. In this process, target ions are extracted into the bulk of the microsphere where they are complexed by the ion-selective ionophores. Influx of positive charge into the microsphere results in deprotonation of the fluoroionophore and a concerted expulsion of a proton from within the microsphere. The equilibrium describing this process is described by Equation 1:

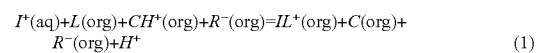

$$I^+(aq)+L(org)+CH^+(org)+R^-(org)=IL^+(org)+C(org)+R^-(org)+H^+ \quad (1)$$

where $I^+$ is the sample ion, L and $IL^+$ are the uncomplexed and complexed forms of the ionophore, respectively, $CH^+$ and C are the protonated and deprotonated forms of the chromoionophore (e.g., a fluoroionophore), respectively, and $R^-$ is the cation-exchanger (1). Parenthetical notations (aq) and (org) denote the aqueous and organic phases, respectively. If the sample pH remains constant (i.e., via buffering), the concerted ion exchange allows for the quantitative determination of the target analyte by measuring changes in the optical activity of the chromoionophore (e.g., fluorescence intensity). Ionophore-mediated sensing strategies are superior to sensing approaches that use surface-attached indicators (6) because of the high selectivity imparted by the ion-detecting microspheres.

Figure 2A:
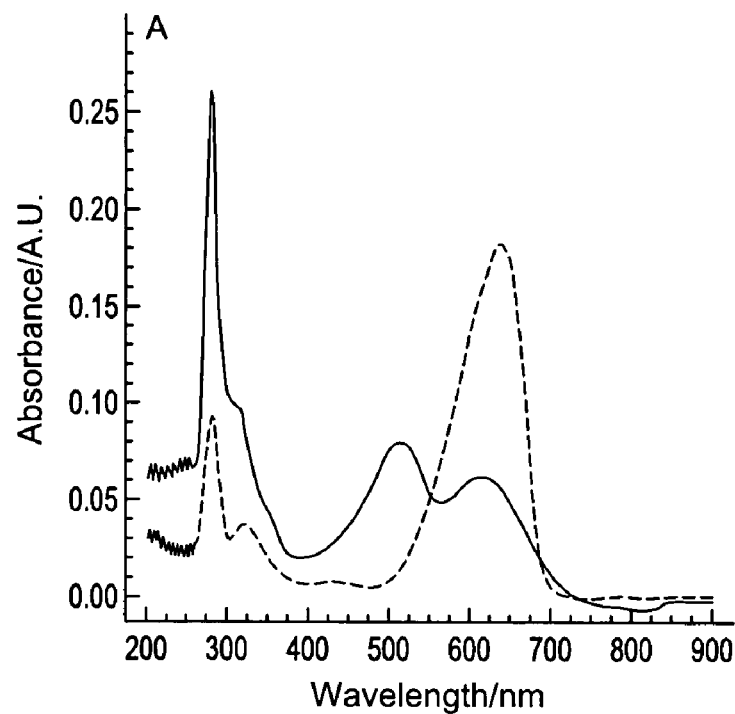
FIG. 2A shows the absorbance of the protonated (dashed line) and deprotonated (solid line) forms of ETH 5294 in DMSO.
Figure 2B:
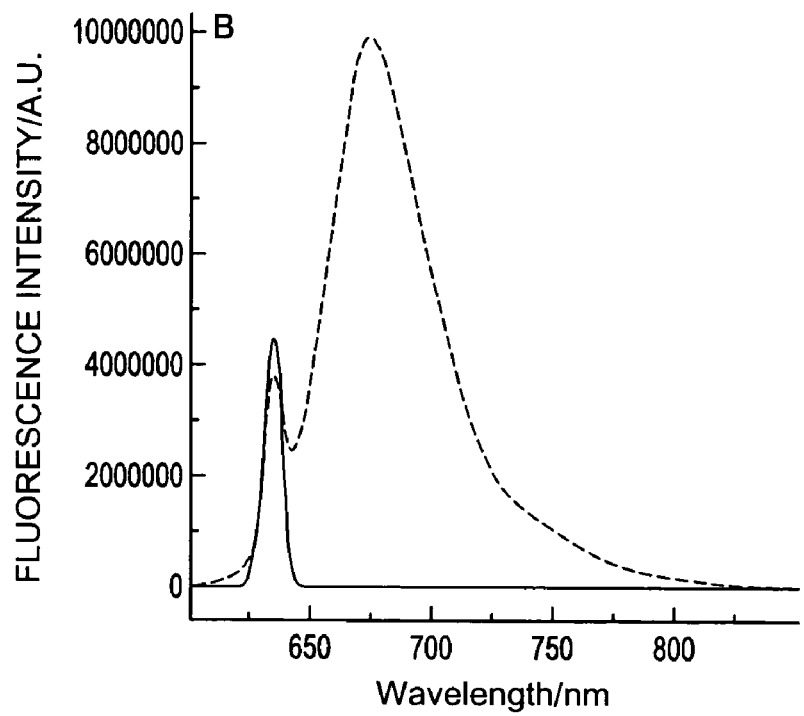
FIG. 2B shows the fluorescence emission characteristics of the protonated (dashed line) and deprotonated (solid line) forms of ETH 5294 ($\lambda_{ex}$=635 nm).

One example of a suitable chromoionophore for purposes of this invention is the fluoroionophore ETH 5294 (30). The absorbance and fluorescence emission characteristics of the ETH 5294 are shown in FIGS. 2A and 2B. In DMSO, the protonated form of ETH 5294 has absorption maxima at 280, 324, and 635 nm, whereas the deprotonated form has maxima at 272, 514 and 615 nm and a shoulder at 305 nm. It is apparent from FIG. 2A that the deprotonated form of the fluoroionophore does not strongly absorb at 635 nm, which may explain the absence of a fluorescence signal for this form of the indicator in FIG. 2B. The protonated form of the fluoroionophore, however, exhibits an emission maximum at 674 nm. When excited at 635 nm, the emission behavior of ETH 5294 is substantially different from that observed when it is excited at 560 nm (17). A loss of ratiometric capabilities results, which is consistent with data reported for another self-referencing fluoroionophore (31). Thus, unlike most fluorescence-based assays, which quantitate a directly proportional relationship between analyte concentration and fluorescence intensity, the approach used according to this invention uses an inverse relationship. That is, an observed decrease in fluorescence correlates to an increase in ion concentration. This can be explained by Equation 1, which shows that the deprotonated form of the fluoroionophore predominates at higher target ion concentrations.

Figure 3:
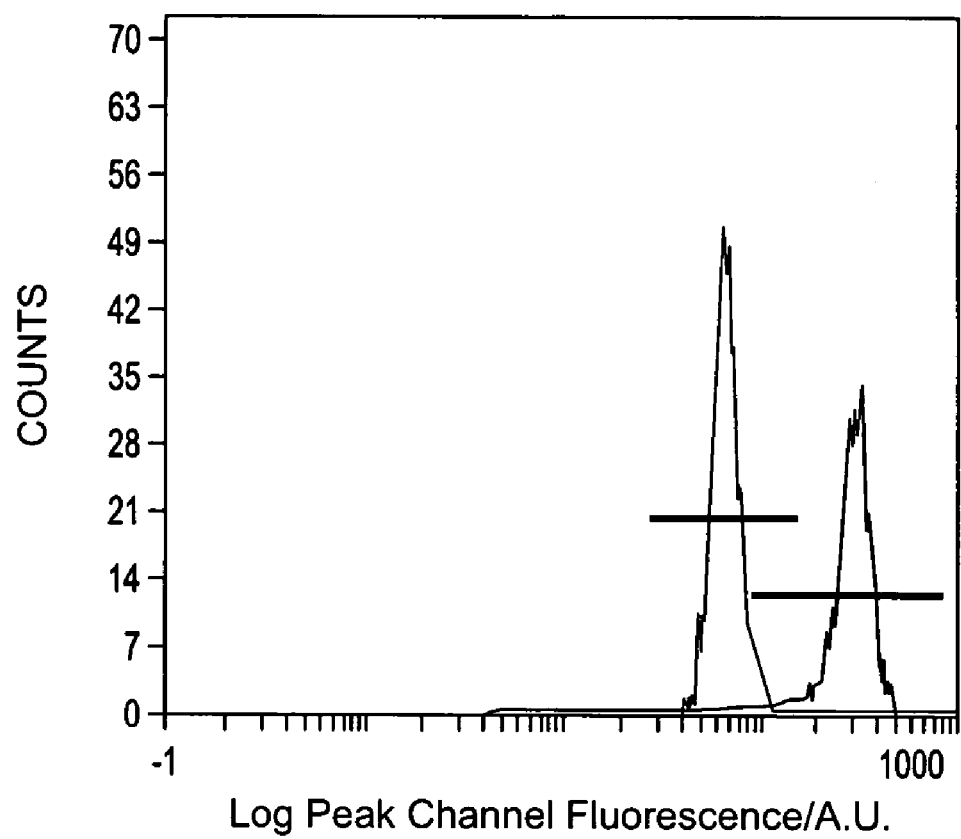
FIG. 3 is a single-parameter histogram depicting peak channel fluorescence intensity variations in type 1 sodium-selective microspheres equilibrated in $10^{-1}$ M (left peak) and $10^{-4}$ M (right peak) sodium samples containing 4 mM Tris, pH 7.4. Horizontal bars represent the full width at half-maximum, from which CVs were determined.

In one embodiment, microspheres selective for either sodium ions or potassium ions were prepared according to the methods described in Example 1. Separate solution analyses of these microspheres resulted in the generation of functional response curves using peak channel fluorescence intensities. FIG. 3 shows a single-parameter histogram depicting peak channel fluorescence intensity variations in type 1 sodium-selective microspheres (see Example 1) equilibrated in $10^{-4}$ M (left peak) and $10^{-4}$ M (right peak) sodium samples containing 4 mM Tris, pH 7.4. This single-parameter histogram shows the number of counts as a function of the log of the peak channel fluorescence. The horizontal distance between the Gaussian curves, which represents sample sodium concentrations of $10^{-1}$ M (left peak) and $10^{-1}$ M (right peak), is indicative of a substantial change in the fluorescence behavior of the fluoroionophore. An increase in target ion concentration results in an increase in the proportion of fluoroionophore in the deprotonated state, which does not emit (see FIG. 2).

Figure 4A:
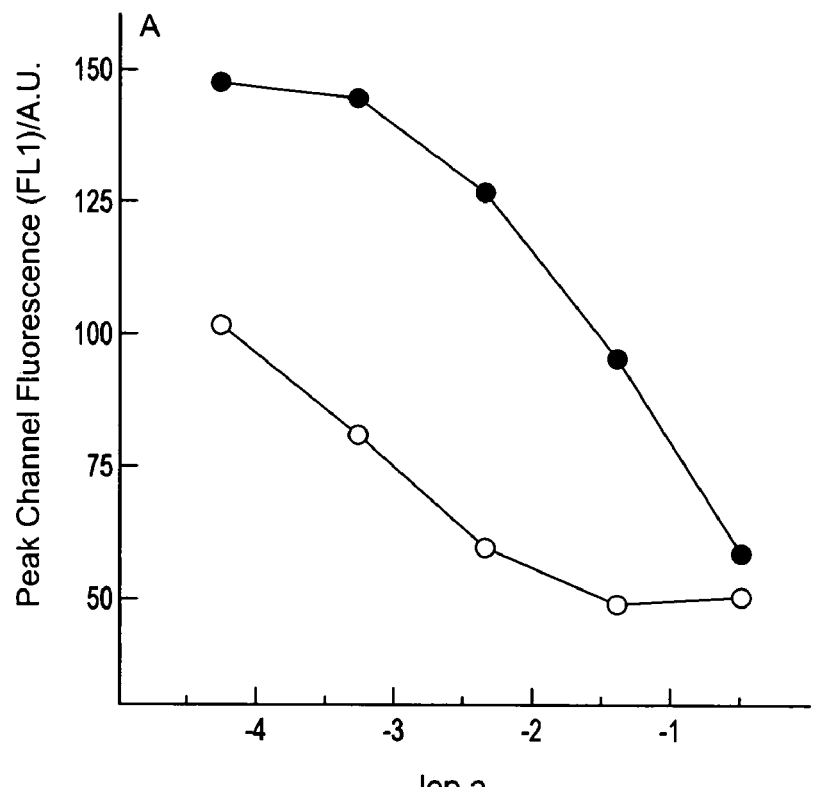
FIG. 4A shows the response and selectivity of type 2 sodium-selective microspheres in sodium (open circles) and potassium (solid circles) sample solutions containing 4 mM Tris, pH 7.4.
Figure 4B:
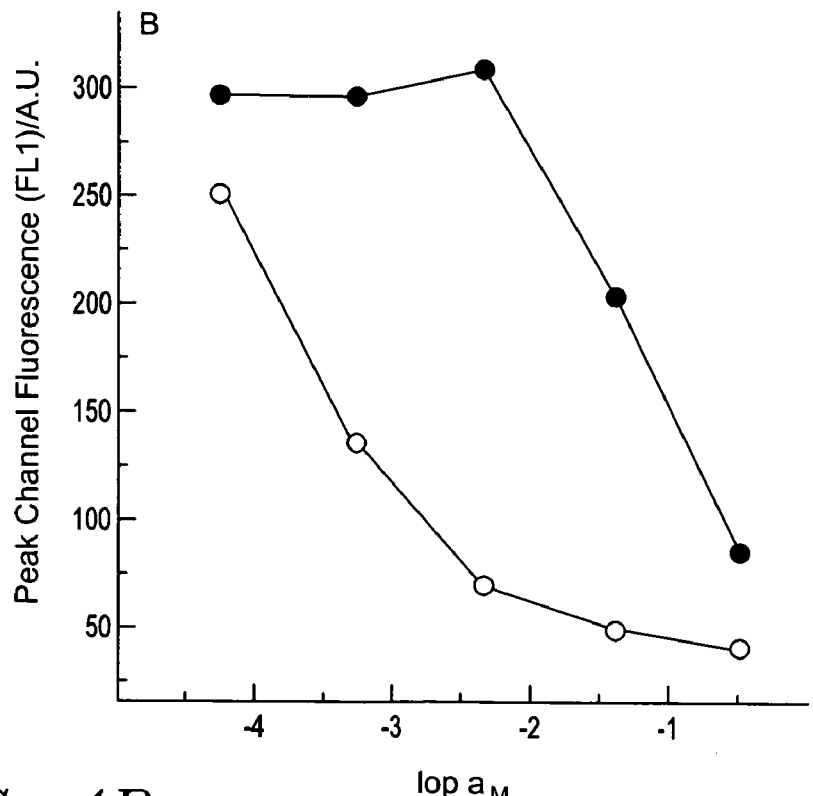
FIG. 4B shows the response and selectivity of potassium-selective microspheres in sodium (open circles) and potassium (solid circles) sample solutions containing 4 mM Tris, pH 7.4.

Response curves depicting the fluorescence changes over a wide range of sample concentrations for sodium ion-sensing microspheres and potassium ion-sensing microspheres are shown in FIGS. 4A and 4B, respectively. Type 2 sodium (i.e., particles containing a higher concentration of sodium ion ionophore X as described in Example 1) were used to generate the curves in FIG. 4A. The data points shown in FIGS. 4A and 4B are the mean values of 2000 sensors. Separate sample solutions were used for each respective ion. It was observed that higher concentrations of potassium were required to deprotonate the fluoroionophore, indicating the selective discrimination of potassium by the sodium ionophore. A parallel shift in the location of the potassium response curve of about 2.5 orders of magnitude is consistent with that previously reported using other detection platforms.

The above results demonstrate that ion-detecting microspheres can be used in conjunction with existing clinical laboratory instrumentation such as flow cytometry as a diagnostic tool for rapid, high-throughput analysis of a sample.

When considering the utility of flow cytometry as a diagnostic tool for the clinical determination of ions, one must consider whether this approach will work for analyzing complex biological fluids. A precursor to that step, however, is the parallel analysis of more than one type of sensor. To test whether the ion-detecting particles of this invention are useful for multiplex analysis, both sodium and potassium-selective particles were suspended in samples containing various sodium ion concentrations. Cytometric analysis of the mixed particle suspension resulted in a single region of particle density on a forward-scatter versus side-scatter plot, which implies homogeneity of particle size (data not shown). The region of particle density was gated and analyzed using FL2 which separated the particle subsets into two distinct regions on the basis of their long-wavelength fluorescence behavior. Because the type 1 sodium particles were also doped with a long-wavelength active dye, particle subsets could easily be segregated. Each particle subset was then gated and analyzed using FL1, which is the fluorescence channel corresponding to the fluorescence signal generated by ETH 5294. The resulting response curves are shown in FIG. 5.

Figure 5:
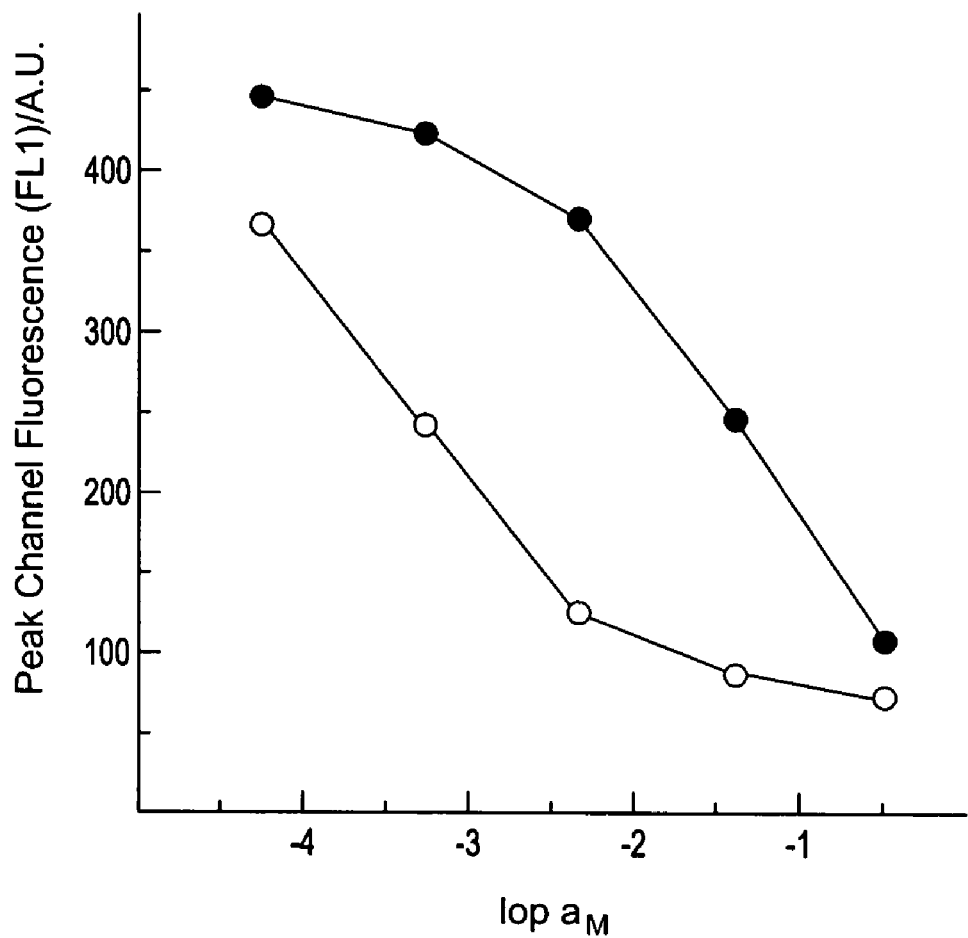
FIG. 5 shows the results of a parallel analysis of type 1 sodium-selective microspheres (open circles) and potassium-selective microspheres in the presence of sodium sample solutions containing 4 mM Tris, pH 7.4.

As shown in FIG. 5, a functional response curve was obtained for sodium (open circles), whereas the curve for potassium (closed circles) is indicative of the selectivity behavior of the potassium ionophore BME-44 over sodium. The selectivity behavior of sodium ionophore X agrees with the results shown in FIG. 4A, in which the microspheres were measured in a serial manner (i.e., each particle subset was measured separately). Preliminary lifetime studies of these microsphere-based sensors have shown that type 2 sodium particles have remained fully functional for periods as long as five weeks. This first step toward the clinical determination of ions lays the foundation for the potential applicability of this technology for the multiplexed analysis of complex biological fluids.

According to another aspect, this invention provides metal ion-selective polymeric microspheres for detecting metal ions in a sample, said microspheres comprising a lipophilic ionophore selective for said metal ions, a chromoionophore selective for hydrogen ions, and a fluorescent dye, wherein said chromoionophore is a chromoionophore that becomes deprotonated when said metal ions in said sample are present, and wherein said deprotonated form of said chromoionophore is absorbent at the frequency of the fluorescence emission of said dye.

Examples of metal ion-selective polymeric microspheres of this invention include microspheres selective for metals such as $Pb^{2+}$, $Cu^{2+}$, $Hg^{2+}$, $Ag^+$, as well as oxides such as $UO_2^{2+}$. The metal ion-selective polymeric microspheres can include any cation exchange-based systems including those for $Pb^{2+}$, $Cu^{2+}$, $Hg^{2+}$, $Ag^+$, $UO_2^{2+}$, such as those reported in the literature (30–34). A preferred lead ionophore is N,N,N',N'-tetradodecyl-3,6-dioxaoctane-1-thio-8-oxodiamide (ETH 5493).

The metal ion-selective microspheres of the present invention further include a chromoionophore. Examples of chromoionophore include, but are not limited to, a pH indicating chromoionophore, a chromoionophore, a fluoroionophore, a pH indicator, or a pH indicating fluoroionophore.

In one embodiment, metal ion-selective microspheres of this invention comprise a lipophilic ionophore selective for lead ions, and a chromoionophore selective for hydrogen ions, incorporated in a polymer matrix. For such a composition, the lead ion activity ($\alpha_{Pb}$) of the microspheres is dependent on the pH of the sample. The lead ion activity is also dependent on the molar concentration of active components, namely, the total concentration of ionophore ($L_T$), the total concentration of chromoionophore ($C_T$), and the total amount of lipophilic anionic sites ($R_T^-$). The value $\alpha$, which corresponds to the relative fraction of unprotonated chromoionophore, is also introduced in the following expression to describe the metal ion activity ($\alpha_1$) in the sample according to Equation 2:

$$\alpha_1 = K_{exch}^{-1} \cdot (\alpha \alpha_H / 1 - \alpha)^z \cdot [(R_T - (1-\alpha) \cdot C_T) / z (L_T - n / z \{R_T - (1-\alpha) \cdot C_T\})^n] \quad (2)$$

where z is the charge of the analyte $I^{z+}$ and n is the ion-ionophore complex stoichiometry. Most typically, the degree of protonation of the chromoionophore (1−α) is used to represent the response function of optode systems in absorbance mode.

Given the need to spatially and spectrally characterize microspheres via fluorescence microscopy, a judicious choice of the chromoionophore is required. The chromoionophore must display appreciable fluorescent quantum efficiency upon pH changes and it should also exhibit a pKa value that permits an effective shift of the dynamic range and detection limit of lead ions to best-suited levels. Furthermore, it must ideally lend itself to ratiometric measurement in order to minimize any possible photobleaching effects and variations in positioning, size and light intensity.

A first chromoionophore explored was the azo-derivative ETH 5315. The $pK_a$ value of ETH 5315 in optode membranes is 5.5 (39), and therefore appeared suitable for detecting lead ions in an acidic media. However, ETH 5315 proved to be unsuccessful, as demonstrated by its very poor fluorescence emission when incorporated in optode films.

Alternatively, the more basic chromoionophore ETH 5418 ($pK_a$ 8.8), which has been used in absorption-based measurements for lead and other heavy metal ions, was investigated as a chromoionophore for the lead ion sensing microparticles of this invention. However, the basic form of ETH 5418 is not light emitting. Therefore, the use of ETH 5418 for fluorescent-based measurements required the development of an "inner filter" approach as follows.

It is known that the fluorescence spectral characteristics of $DiIC_{18}$ (a lipophilic dye) can be modulated by the absorption changing properties of more basic chromoionophores (14).

Accordingly, $DiIC_{18}$ was added to the formulation containing the basic chromoionophore ETH 5418 for the production of the lead ion selective microparticles of this invention. It was discovered that the basic form of the chromoionophore ETH 5418 absorbs strongly in the region where the reference dye $DiIC_{18}$ is fluorescent but where the acidic form of the chromoionophore exhibits no spectral characteristic.

Figure 6:
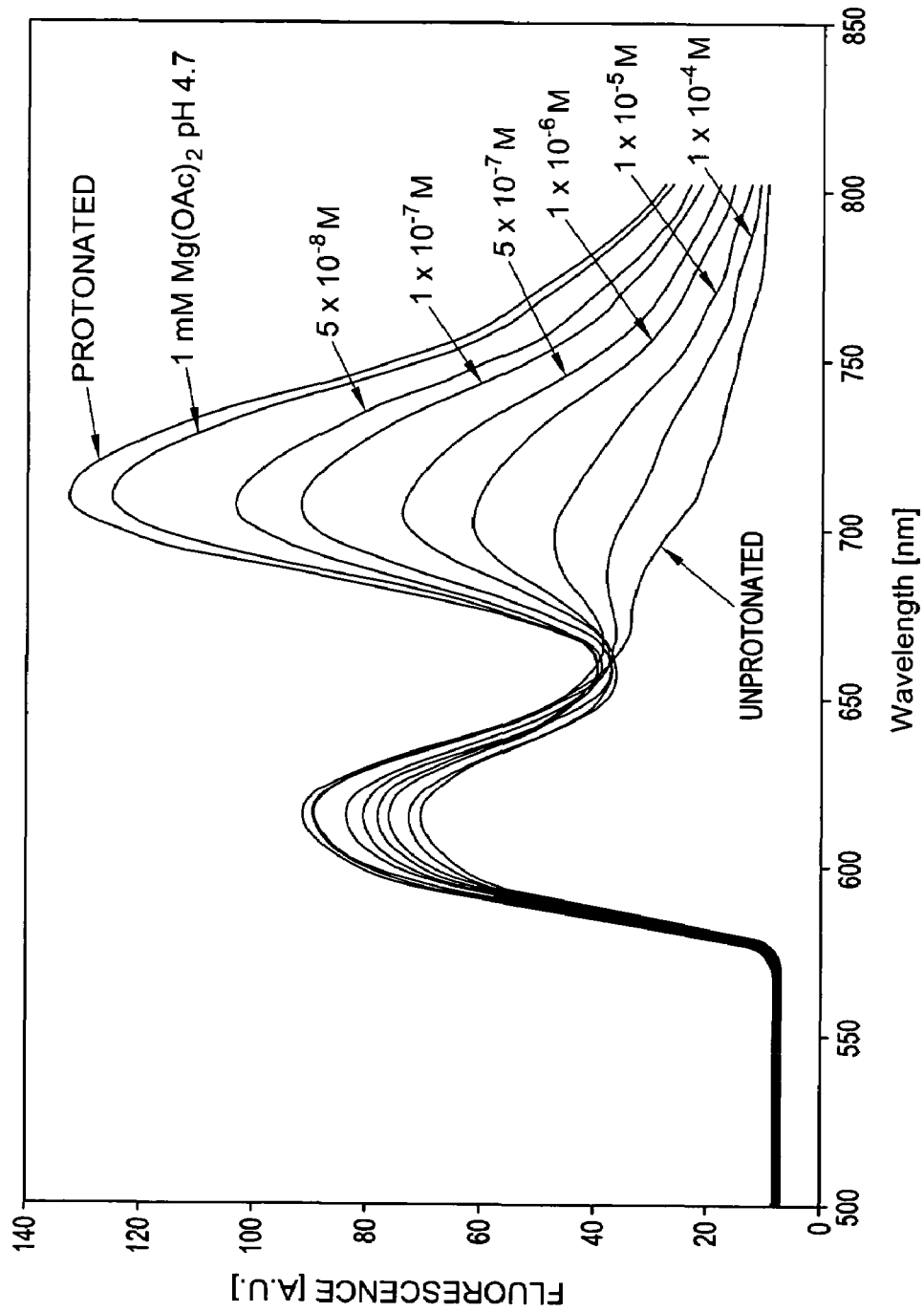
FIG. 6 is the fluorescence spectra of a lead ion-selective optode film after equilibration with different lead concentrations in Mg(OAc)$_2$ buffer at pH 4.6. The optode film contains lead ionophore Pb-IV, NaTFPB, DOC, PVC, and the ETH 5418 chromoionophore (basic form 717 nm) modulating the fluorescence emission of the lipophilic DiIC$_{18}$ dye (617 nm).

FIG. 6 shows the spectral fluorescence response of an optode film prepared with microspheres containing the chromoionophore ETH 5418, the modulator dye $DiIC_{18}$, the lead ionophore Pb-IV and the ion exchanger TFPB as a function of various lead ion concentrations in $Mg(OAc)_2$ buffered sample at pH 4.7. As seen from FIG. 6, the ETH 5418-$DiIC_{18}$ pair lends itself nicely to spectral resolution of both emission peaks. As deprotonation of ETH 5418 (717 nm) occurs in response to lead activity in the sample the absorbance of its basic form increases sharply. As a consequence of the overlap with the emission spectrum of $DiIC_{18}$, the emission of the $DiIC_{18}$ decreases appropriately.

Since the basic form of the chromoionophore is absorbent at the frequency of the fluorescence emission of the $DiIC_{18}$, the fluorescence intensity of the dye decreases as deprotonation of 5418 increases in response to an increase of lead ion concentration. Thus, the degree of protonation of the fluorescent chromoionophore is described as a function of the observed fluorescence ratios as shown in Equation 3:

$$1-\alpha = [IndH^+]/Ind_T = 1-[1+((R_{max}-R)/R-R_m)]^{-1} \quad (3)$$

where R, and $R_{min}$, and $R_{max}$ are the fluorescence intensity ratios for a given equilibrium and at maximum and minimum protonation of the chromoionophore (10).

The lead ion-detecting microspheres whose response is depicted in FIG. 6 were prepared with the casting apparatus as described in Example 3, in which a batch of PVC-DOS plasticized particles of equal composition to the optode film incorporated the lead ionophore Pb-IV and the ETH 5418 chromoionophore. However, although single particles were obtained whose shape, size and acid-base response were as expected, exposure to dilute buffer solutions resulted in complete or partial deprotonation of the chromoionophore, thus yielding irreproducible results. The very high selectivity coefficients of Pb-IV ionophore reported for polymeric membranes of ISEs (36) supported the fact that interference by buffer ions was unlikely. Instead, the loss of Pb-IV ionophore during the casting process was the most likely explanation. Efforts to greatly increase the concentration of Pb-IV ionophore were hindered by the limited solubility of Pb-IV ionophore in DOS plasticizer. Indeed, films containing about 20 mmol/kg of ionophore where observed to crystallize in the membrane over time.

Recent reports on the use of Pb-IV ionophore in membranes of ISEs plasticized with o-NPOE demonstrating lead ion response in the nanomolar concentration level (40) prompted the formulation of batches with this plasticizer. However, in this case such efforts were met with the inability to deprotonate the chromoionophore, which may be indicative of near-complete leaching of the more-polar plasticizer (the particle produced were significantly smaller than with DOS under the same conditions).

As a result of these initial studies, the lead ion-selective ionophore ETH 5493 (37) was investigated as an ionophore for the lead ion-detecting microspheres of this invention. Since the solubility of this ionophore in various plasticizers is not a problem at high concentrations, particle batches as described in Example 3 were prepared. Optical ion exchange constants (Equation 1) and selectivity coefficients for particles prepared by incorporating this ionophore were determined for some relevant ions. The results are shown in Table 1 (complex stoichiometries are from the reference (37)). As shown, the particles display excellent selectivity characteristics, which is in line with earlier described data (37).

TABLE 1

Selectivity of lead-selective microsphere sensing particles.[a]

| Ion | z | n[b] | $log^K_{exch}$ | $log^K_{IJ}{}^{opt}$ |
|---|---|---|---|---|
| $Pb^{2+}$ | 2 | 2 | −2.3 | 0 |
| $Na^+$ | 1 | 1 | −3.6 | −5.2 |
| $Ca^{2+}$ | 2 | 2 | −7.0 | −10.9 |
| $Cd^{2+}$ | 2 | 2 | −1.2 | 1.0 |
| $K^+$ | 1 | 1 | −3.5 | −5.1 |

[a]Procedure according to the references. (30, 41)
[b]n is the assumed complex stoichiometry (37) and $K_{exch}$ the experimentally determined ion-exchange constant for the listed ion (see eq 1).

Figure 7:
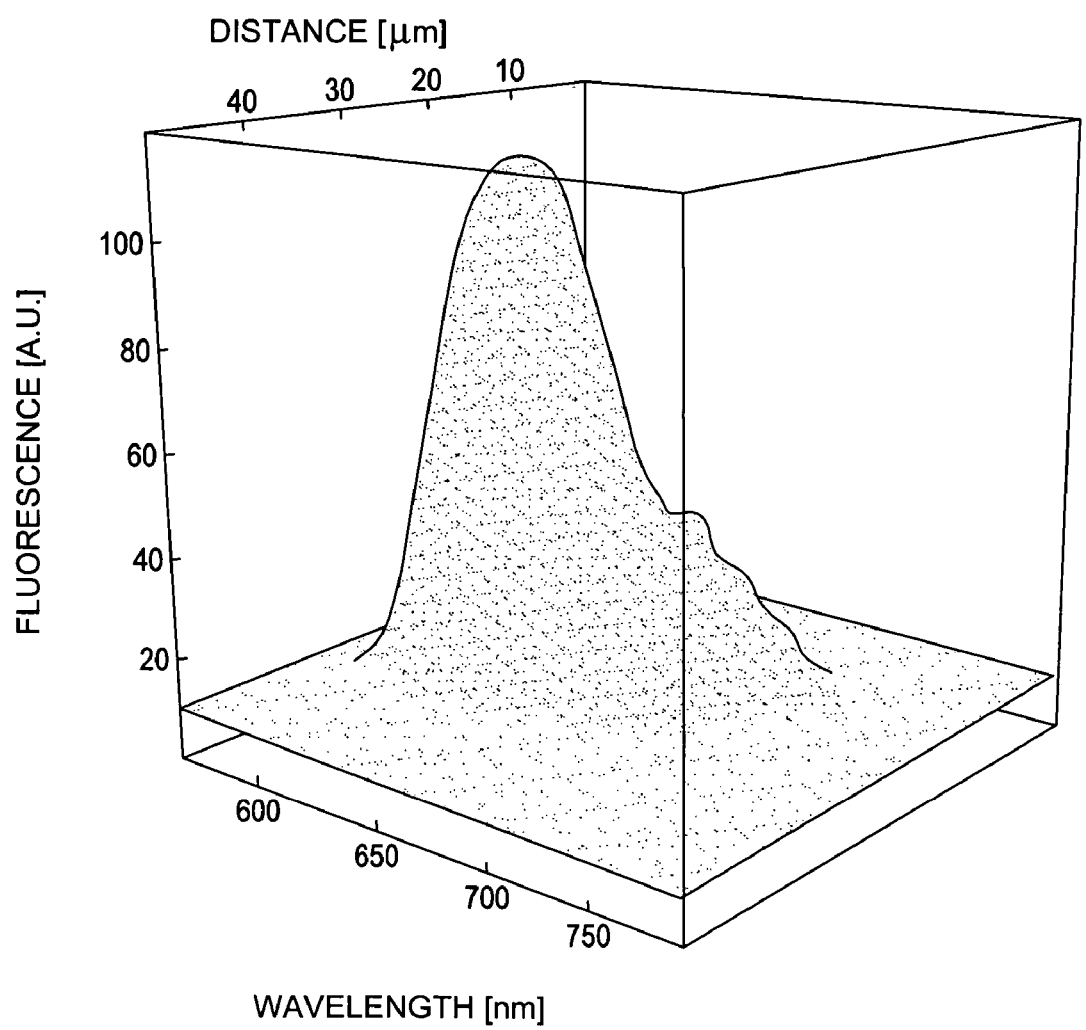
FIG. 7 is the spatially resolved fluorescence spectrum of a single sensing lead particle in its deprotonated form as observed with a fluorescence spectrophotometric microscope. The spatial position of highest fluorescence intensity marks the middle of the microsphere.

FIG. 7 depicts a typical spatially resolved fluorescence spectrum obtained from a single lead ion-detecting microsphere with the chromoionophore ETH 5418 in its deprotonated form, lead ionophore ETH 5493 (87.2 mmol/kg), chromoionophore ETH 5418 (10.2 mmol/kg), ion-exchanger NaTFPB (23.8 mmol/kg), and reference dye DiIC18 (6.9 mmol/kg) in PVC plasticized with DOS in a 1:2 ratio by weight. The particles were found to be uniform in size and spherical, and their surface appeared smooth under the microscope.

Figure 8:
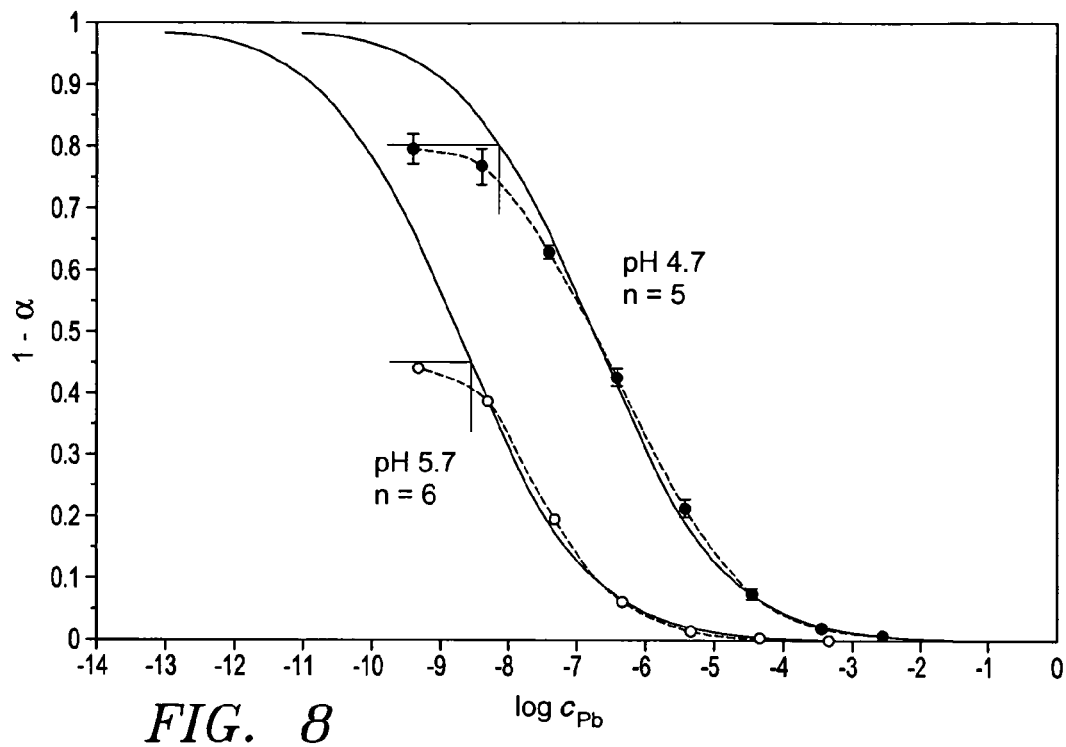
FIG. 8 shows the response function of single sensing particles to Pb(NO$_3$)$_2$ solutions in Mg(OAc)$_2$ buffer at pH 4.7 (closed circles) and pH 5.7 (open circles). Dashed lines indicate the detection limit at each pH calculated according to reference 42. Both curves were generated with log K$_{exch}$ of −2.4.

FIG. 8 shows typical responses of the lead ion-detecting microspheres (same formulation as described with respect to FIG. 7) obtained for lead ion concentrations ranging from $5 \times 10^{-10}$ to $5 \times 10 M^{-3}$ at pH 4.7 and pH 5.7. As shown, the particles responded with a high degree of sensitivity and in full agreement of the expected theoretical values calculated on the basis of Equation 3. Furthermore, the results emphasize the excellent particle-to-particle reproducibility that is obtained via the particle casting method, as the relative standard deviation of the measurements is within a few percent (see error bars in FIG. 8).

Figure 9:
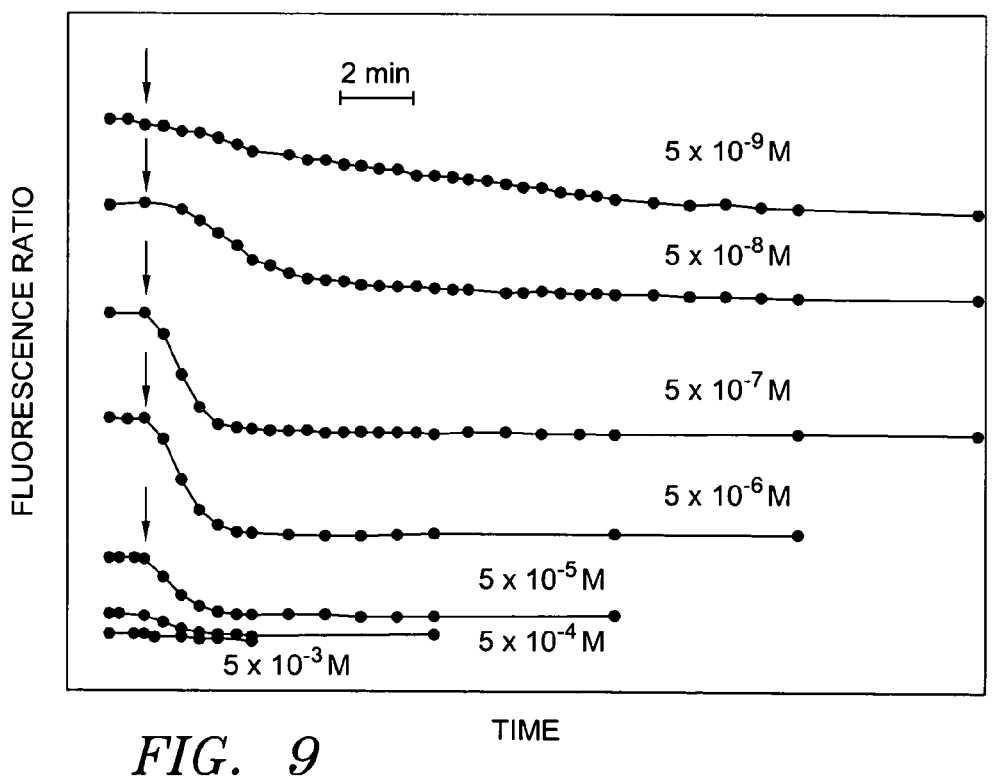
FIG. 9 shows the response time behavior for a single sensing particle immobilized in a capillary flow cell at different lead concentrations at pH 4.7. Arrows indicate the moment of injection as lead solutions of smaller concentrations flow past the particles until equilibration of the signal is achieved.

FIG. 9 shows typical response times of a single lead ion-detecting microsphere (same formulation as described with respect to FIG. 7) immobilized in a glass capillary cell and assessed in the flowing stream of test samples containing lead ions. The arrows in FIG. 9 represent the apparent moment of injection in which the sensing particle first transitions from lower to higher concentrations of lead. As seen in FIG. 9, the equilibrium response time for a 13 μm particle at lead ion concentrations of $5 \times 10^{-3}$ M and higher is reached essentially in 2.5 minutes. For concentrations at detection limit levels, that is, about $5 \times 10^{-9}$ M, the time needed for complete response is about 15 minutes. FIG. 9 also illustrates the high response stability observed for the various concentration changes, thus indicating minimum or negligible drift following multiple exposures to the light source.

Equilibrium response values on the order of minutes as demonstrated by the lead ion-detecting microspheres of this invention represent a considerable enhancement over the response time behavior of optode films, which have been found to exhibit extremely long response times in highly diluted samples. Indeed, optode membranes proposed earlier for the analysis of $Pb^{2+}$ at the nanomolar level necessitated hours of equilibration for stable signals to be obtained (30). More recently, optode systems developed for other environmentally relevant ions e.g., $Ag^{2+}$ have also been shown to require response times in excess of few hours at detection limit levels or tens of minutes for higher concentrations. As the rate-limiting step in optode films in contact with dilute solutions is thought to depend on the convective mass transport to the membrane, the saturation of the bulk equilibrium is expected to be massively shortened for micron-size particles of the type described herein. Such behavior clearly arises from the drastically reduced amount of active components found within the particle. Indeed, a 10 µm particle requires only on the order of $2\times10^{-11}$ mol lead ions to reach an accurate optical response (at $\alpha$=0.5), which is a full 4 orders of magnitude smaller than with traditional thin films. This exemplifies one of the benefits of miniaturization of this powerful chemistry.

The ion-detecting microspheres of the present invention may be used for detecting ions of all types of body fluid samples. Examples of the samples include, but are not limited to, whole blood, spinal fluid, blood serum, urine, saliva, semen, tears, etc. The fluid sample can be assayed neat or after dilution or treatment with a buffer.

The ion-detecting microspheres of the present invention may also be used for detecting ions of all types in environmental samples such as water.

Additional features and advantages of this invention shall be set forth in part in the description that follows, and in part will become apparent to those skilled in the art upon examination of the following specification or may be learned by the practice of the invention. The advantages and novel features of this invention may be realized and attained by means of the instrumentalities, combinations, and methods particularly pointed out in the appended claims.

EXAMPLES

The following reagents were used in the examples described below. Poly(vinyl chloride), (PVC), bis(2-ethylhexyl) sebacate (DOS), tert-butylcalix[4]arene tetraethyl ester (sodium ionophore X), 2-dodecyl-2-methyl-1,3-propanediyl bis[N-[5'-nitro-(benzo-15-crown-5)-4-yl]carbamate (potassium ionophore III, BME-44), 9-(diethylamino)-5-octadecanoylimino-5H-benzo[a]phenoxazine (chromoionophore 1, ETH 5294), and sodium tetrakis-[3.5-bis(trifluoromethyl)phenyl]borate (NaTFPB), 4-tert-butyl-calix[4]arene-tetrakis(N,N-dimethylthioacetamide) (lead ionophore IV), 11-[(-butylpentyl)oxy]-11-oxoundecyl4-[9-(dimethylarmino)$_5$H-benzi[a]phenoxazin-5yl-idene] aminobenzoate (ETH 5418, chromoionophore VII), 4-[[9-dimethylamino]-5H-benzo[a]phenoxazin-5ylidene]amino] benzeneacetic acid 11-[(1-butyl-pentyl)oxy]-11-oxoundecylester (ETH 2439 chromoionophore II), and tetrahydrofuran (THF) were Selectophore quality from Fluka (Milwaukee, Wis.).

The ring-locked cyanine (RLC) reference dye 2-[2-[2-chloro-3-[(1,3-dihydro-3,3-dimethyl-1-decylbenzoindol-2-ylidene)ethylidine]-1-cyclohexn-1-yl[ethenyl]-3,3-dimethyl-1-decylbenzoindoliumn iodide was obtained from Beckman Coulter, Inc. (Brea, Calif.). Dichloromethane (DCM) (EM Sciences), xylenes (EM Sciences), cyclohexanone (JT Baker), and diethyl sulfoxide (DMSO) (Aldrich) were ACS grade and were obtained from the indicated suppliers. Chloride salts of sodium and potassium were reagent grade and were obtained from Mallinckrodt and Sigma, respectively. Tris(hydroxymethyl)amino methane (Tris) was reagent grade from Sigma. A reverse-osmosis water filtration system (US Filler, Philadelphia, Pa.) was used to distill and deionize the water (18 MΩ) from which sample solutions were prepared.

The nitrate salts of lead, cadmium, copper, silver, mercury and the chloride salts of sodium, potassium and magnesium were all puriss. p.a. from Fluka. The internal reference dye 1,1"-dioctadecyl-3,3,3',3'-tetramethylindocarbocyanine perchlorate (DiIC$_{18}$) was from Molecular Probes (Eugene, Oreg.), cyclohexanone (99.8%) was from Aldrich, and dichloromethane and xylenes (ACS grade) were from Fisher. The 4-(octadecylamino)azobenzene (chromoionophore ETH 5315) was synthesized according to a published procedure (14). The N,N,N',N'-tetradodecyl-3,6-dioxaoctane-1-thio-8-oxodiamide (ETH 5493) ionophore was a gift from the laboratory of Prof. E. Pretsch (ETH, Zurich), which had been synthesized as described (37).

Example 1

Preparation of Ion-Detecting Microspheres

A polymer cocktail containing PVC, DOS, ionophore, ETH 5294 and NaTFPB was dissolved in 5 mL of cyclohexanone and diluted with 100 mL of dichloromethane. The addition of 1 mL of xylenes to the solution aided in the aesthetic appearance of the cast particles. Potassium sensing microspheres contained PVC (33 wt %), DOS (66 wt %), ETH 5294 (0.2 mmol/kg), NaTFPB (0.3 mmol/kg), and the potassium ionophore BME-44 (21.1 mmol/kg). Sodium sensing microspheres contained PVC (33 wt %), DOS (66 wt %), ETH 5294 (0.2 mmol/kg), and either sodium ionionophore X (10.0 mmol/kg) and NaTFPB (0.3 mmol/kg) (type 1) or sodium ion-ionophore (89.3 mmol/kg) and NaTFPB (27.1 mmol/kg) (type 2). For segregation of particle subsets in the parallel analyses, type 1 sodium sensing particles also contained RLC reference dye ($3.9\times10^{-3}$ mmol/kg). Particles were prepared using a particle casting apparatus as described by Tsagkatakis et al. (16).

The following settings and specifications were used in this example: tip diameter: 38.1 µm; frequency, 21.S kHz; polymer flow rate, 0.5 mL/min: water flow rate, 52 mL/min: surfactant flow rate, 1 drop/10 s; curing duration, 4 days. The surfactant was added using a model 352 syringe pump (Sage Instruments, Boston, Mass.).

Example 2

Instrumentation and Measurement

The absorption behavior of ETH 5294 in both its protonated and deprotonated forms was determined using a DU 70 spectrophotometer (Beckman Coulter, Inc., Fullerton, Calif.). For fluorescence characterization, a $1\times10^{-5}$ M solution of ETH 5294 in DMSO was mixed with a 1% (v/v) aqueous solution of either HCl or NaOH and excited at 635 nm using a Fluorolog 3 fluorometer (Instruments SA, Edison, N.J.) to determine the emission behavior of the protonated and deprotonated forms at this wavelength. Optical characterization of RLC in methanol found $\lambda_{ex}$=820 nm and $\lambda_{em}$=860 nm.

A Beckman Coulter EPICS XL flow cytometer modified for both 635-nm and 785-nm excitation was used to interrogate the sensing microspheres. A 650-nm long-pass emission filter and a 660 (±15) nm band-pass filter were used to collect fluorescence emitted between 650 and 675 nm, and an 800-nm long-pass emission filter was used to collect fluorescence emitted above 800 nm. A schematic representation illustrating the optical setup of the cytometer that was used appears in FIG. 1. The sensing microspheres were equilibrated for 30 seconds in sodium or potassium sample solutions containing 4 mM Tris buffer, pH 7.4.

Example 3

Preparation of Lead Ion-Detecting Microspheres

The schematic set-up and the general protocol for the preparation of sensing particles have been reported recently (17) and it applies here with minor modifications. Unless otherwise indicated a cocktail mixture was prepared by weighing out 58.5 mg PVC, 116 mg DOS, 1.44 mg (10.2 mmol/kg) chromoionophore, 1.27 mg (6.9 mmol/kg) reference dye DiICI8, 4.05 mg (23.8 mmol/kg) ion exchanger NaTFPB, 14.8 mg (87.2 mmol/kg) ionophore and dissolving it in 5 mL of cyclohexanone. The mixture was shaken in a vortex mixer for approximately one hour and then added dropwise to 100 mL dichloromethane under gentle stirring. After adding 1 mL xylenes the solution was filtered through a 0.45 µm Gelman filter and 50 mL transferred to a gas-tight Hamilton syringe. The syringe containing the polymer core solution was mounted on a syringe pump (Stoelting, Wood Dale, Ill.) and set to flow at a rate of 0.263 mL min$^{-1}$. Deionized water used as the sheath liquid stream flowing at a rate of 43 mL/min was controlled via a pressure regulator. The frequency generator was operated at a setting of 12.3–12.7 kHz.

Example 4

Instrumentation for Analyzing Lead Ion-Detecting Microspheres

A Pariss Imaging Spectrometer (Light Form, Belle Mead, N.J.) combined with a Nikon Eclipse E400 microscope with an epifluorescence attachment (Southern Micro Instruments, Marietta, Ga.) was used to optically characterize optode films and particles. The system was equipped with two CCD cameras EDC 1000L (Electrim Corp., Princeton, N.J.) and a Nikon super high-pressure mercury arc lamp (Southern Micro Instruments). A filter cube with a 510–560 nm excitation filter, a 565 nm dichroic mirror, and a 590 nm long pass emission filter was used. The system, equipped with a motorized stage (Prior Optiscan ES9, Fulbourn, Cambs, UK.) was operated via Pariss data acquisition software, to record individual fluorescence spectra of particles and films under the field of view. The schematic representation of this optical arrangement has been reported previously (17).

Example 5

Measurements of Lead Ion-Detecting Microspheres

Particles were collected in 20 mL small glass vials directly from the emerging jet of the casting apparatus. A 100 µL aliquot of liquid containing resuspended particles was deposited on a 22 mm wide Fisherbrand® microscope cover glass immediately after collection and allowed to evaporate in the dark under a hood draft. After evaporation, the glass substrate containing immobilized particles was mounted into a flow cell, fitted on the motorized stage of the microscope and connected to a small peristaltic pump (Dakota Instruments). Fluorescence spectra were taken under static conditions and after equilibrating the flow cell with given test concentrations. For response time measurements, a borosilicate glass microcapillary cell of 1.0 mm i.d. and 0.15 mm wall thickness was used in order to reduce the dead volume. A 50 µL aliquot of collected particles was pipetted inside the capillary cell and the liquid was left to evaporate under gentle vacuum. The capillary was positioned over a glass fixture, attached at each end with polyethylene tubing and connected to a peristaltic pump operated at a rate of 0.1 mL/min. Measurements were taken every 30–60 seconds for 5 minutes and every minute or longer thereafter. In all cases, the image of a particle was obtained using a 40×-microscope objective to capture a specific slice under the field of view, typically using transmission mode to avoid photobleaching. The spectral image of this slice was then taken in the fluorescence mode. For all measurements neutral density filters 4 and 8 were used to decrease the light intensity from-the source. Exposure time for spectral acquisition of particles was 500 ms and for films 300 ms.

Standard $5 \times 10^{-3}$ M stock solutions were prepared by dissolving the metal salt in a 1 mM magnesium acetate buffer of desired pH. Test solutions were then prepared by stepwise gravimetric dilution with the same buffer. For concentrations below $10^{-7}$ M, aliquots of the $10^{-6}$ M solution were diluted with increasing volumes of buffer to give the final concentration. Calibrating solutions were all prepared in polyethylene beakers that had been pretreated with 0.01 M $HNO_3$.

Example 6

Preparation of Optode Films Comprising Lead Ion-Detecting Microspheres

For optode film preparation, ion-exchanger salt additive (7.4 mmol kg$^{-1}$), lead ionophore (13 mmol kg), chromoionophore ETH 5418 or ETH 2439 (6.5 mmol kg$^{-1}$), internal reference dye DiIC$_{18}$ (5.4 mmol kg$^{-1}$), plasticizer and PVC (2:1 by weight) were weighed out and dissolved in 1.5 mL THF. After complete dissolution, the sensing cocktail was spin coated onto quartz glass plates and any remaining solvent was left to evaporate in a hood draft for at least 30 minutes prior to measurements.

Results and Discussion

Uniform, monodisperse ion-detecting microspheres were prepared from plasticized PVC using a high-throughput particle casting technique (16). In one embodiment, the particles incorporated with an ionophore having high selectivity for the target ion, and a neutral hydrogen-ion fluorophore.

Cytometric measurement of the fluorescence intensities from individual particles produces a coefficient of variation (CV) in the estimate of the mean fluorescence equal to the CV of the particle population. The CV in the estimate of the mean can be improved by averaging the measurements from multiple particles. Repeat subsampling of a read of 10,000 particles gave precision improvement consistent with Polson statistics. For mean peak fluorescence channel values of 109.3, the CV in the estimate of the mean improved from 12.5% to 1.2% to 0.4% when the sample size was increased from 1 to 300 to 1000, respectively. Conversely, potassium-selective particles containing the ionophore BME-44 demonstrate function and selective discrimination of sodium ions as shown in FIG. 4B. The selectivity observed, which is indicated by the 2.5 orders of magnitude parallel shift of the sodium response curve, is consistent with the particle-based detection method described by Tsagkatakis et al. (17).

When dealing with biological samples, a primary concern is the biasing of results due to sample autofluorescence. This obstacle may be circumvented by judiciously selecting a fluoroionophore that has appropriate spectral characteristics and by using long-wavelength excitation. Under these circumstances, the emission behavior of the sensing ionophore is usually beyond the wavelength range over which autofluorescence typically occurs (3). Furthermore, encoding dyes such as RLC and optical filters may also be used to eliminate undesired fluorescence wavelengths.

The precision of microsphere-based flow cytometry is ultimately contingent upon the monodispersity of the particles. The particle fabrication method used herein has been reported to produce uniform particles with a diameter variation of 1.5% (32). Furthermore, CVs representing the particle-to-particle reproducibility of fluorescence flow cytometric measurements have been reported to be as low as 3.6% (32), although this signal variation may appear to be a potential limitation of this technique, ratio metric capabilities of the readout will greatly improve reproducibility. Moreover, the ease of measurement of the numbers of particles makes excellent precision possible, even with poor particle uniformity.

Implementation of microsphere-based technologies for ion analyses makes it possible to use existing instrumentation commonly found in the clinical laboratory to determine this class of analytes. A suitable technique that is commonly used for microsphere-based assays is flow cytometry. Flow cytometry offers a means for high-throughput screening, which is a capability not found with microscopic techniques. This is primarily due to differences in the detectors commonly employed with each technique. In fluorescence microscopy, charge-coupled devices that offer excellent spatial and temporal resolution are typically used, however these devices suffer from longer data acquisition times on the order of the millisecond time scale. Flow cytometry, on the other hand, uses photo-multiplier tubes, which allows for measurements to be collected on the microsecond time scale (29). This inherent advantage in conjunction with multiplexed measurement capabilities makes flow cytometry an attractive analytical method for clinical applications.

Conclusion

This invention demonstrates the applicability of flow cytometry as a means for developing multiplexed, rapid, high-throughput analyses for clinically relevant ions. In one embodiment, ionophore-mediated microsphere-based sensors selective for sodium and potassium were prepared using a high-throughput particle casting apparatus that utilizes a sonic droplet formation process. Flow cytometry was demonstrated to be a useful analytical detection platform for the analysis of sample ion concentrations. The ion sensing microspheres were analyzed serially and in parallel via long-wavelength flow cytometry and were shown to possess acceptable sensitivity, selectivity, and precision for the potential clinical determination of these ions.

In another example, fluorescent plasticized PVC microspheres incorporating a selective ionophore for lead metal ions were prepared via a casting apparatus that allows for the mass production of highly reproducible spherical particles. Immobilized particles assayed in a flowing stream of analyte were imaged via fluorescence spectroscopy and shown to follow predicted theory, allowing lead ion determinations at the low nanomolar level. Responses were characterized by high stability and reproducibility with a detection limit comparable to those found for optode films. However, in contrast to optode thin films that require typical equilibration times of hours following exposure to nanomolar level concentrations, the particles prepared here were shown to respond rapidly in just a few minutes and required drastically reduced sample volumes on the order of one milliliter. Miniaturized ionophore-based sensing microspheres are therefore a very promising platform for the assessment of trace level concentrations in a variety of samples.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes, which come within the meaning and range of the equivalence of the claims, are to be embraced within their scope.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

REFERENCES

1) Bakker, E.; Buhlmann, P.; Pretsch, E. *Chem. Rev.* 1997, 97, 3083.
2) Buhlmann, P.; Pretsch, E.; Bakker, E. *Chem. Rev.* 1998, 98, 1593.
3) Clark, H. A.; Barker, S. L. R.; Brausuel, M.; Miller, M. T.; Monson, E.; Parus, S.; Shi, Z-Y.; Song, A.; Thorsrud, B.; Kopelman, R.; Ade, A.; Meixner, W.; Athey, B.; Hoyer, M.; Hill, D.; Lightle, R.; Philbert, M. A. *Sens Actuators, B* 1998, 51, 12.
4) Clark, H. A.; Kopelman, R.; Tjalkens, R.; Philbert, M. A., *Anal. Chem.* 1999, 71, 4837.
5) Clark, H. A.; Hoyer, M.; Philbert, M. A.; Kopelman, R. *Anal. Chem.* 1999, 71, 4831.
6) Goodey, A.; Lavigne, J. J.; Savoy, S. M.; Rodriquez, M. D.; Curey, T.; Tsao, A.; Simmons, G.; Wright, J.; Yoo, S. J.; Sohn, Y.; Anslyn, E. V.; Shear, J. B.; Nelkirk, D. P.; McDevitt, J. T. *J. Am. Chem. Soc.* 2001, 123, 2559.
7) Hakala, H.; Lonnberg, H. *Bioconjugate Chem.* 1997, 8, 232.
8) Hakala, H.; Heinonen, P.; Iitia, A.; Lonnberg, H. *Bioconjugate Chem.* 1997, 8, 378.
9) Koronczi, I.; Reichert, J.; Helnzmann, G.; Ache, H. J. *Sens. Actuators, B* 1998, 51, 188.
10) Kurihara, K.; Ohtsu, M.; Yoshida, T.; Abe, T- Hisamoto, H.; Suzuki, K. *Anal. Chem.* 1998, 71, 3558.
11) Niehren, S.; Kinzelbach, W.; Seeger, S.; Wolfrum, J. *Anal. Chem.* 1995, 67, 2665.
12) Nanthakumor, A.; Pon. R. T.; Mazumder, A., Yu, S.; Watson, A. *Bioconjugate Chem.* 2000, 11, 282.
13) Peper, S.; Tsagkatakis, I,; Bakker, E., *Anal. Chim. Acta* 2001, 42, 25.
14) Shortreed, M.; Bakker, E.; Kopelman, R. *Anal. Chem.* 1996, 68, 2656.
15) Shortreed, M. R.; Dourado, S.; Kopelman, R. *Sens. Actuators. B* 1997, 38–39, 8.
16) Tsagkatakis, I.; Peper, S.; Retter, R.; Bell, M.; Bakker, E. *Anal. Chem.* 2001, 73, 6083.
17) Tsagkatakis, I.; Peper, S.; Bakker, E. *Anal. Chem.* 2001, 73, 315.
18) Lubbers, D. W.; Opitz, N.; Spelser, P. P.; Bisson, H. J. Z. *Naturforsch. C. J. Biosci.* 1977, 32, 133.
19) Brasuel, M.; Kopelman, R.; Miller, T. J.; Tjalkens, R.; Philbert, M. A. *Anal. Chem* 2001, 73, 2221.
20) Kim, S. B.; Cho, H. C.; Cha. C. S.; Nam, H.; *Anal. Chem.* 1998, 70, 4860.

21) Fulwyler, M. J.; Coulter Electronics, Inc.; U.K. Patent 1,561,042, 1975.
22) Fulton, R. J.; McDade, R. L.; Smith, P. L.; Kienker, L. J., Jr.; J. R. K. *Clin. Chem.* 1997, 43, 1749.
23) Kerrrman, J. R.; Davies, T.; Chandler, D.; Oliver, K. G.; Fulton, R. J. *Cytometery,* 1998, 33, 234.
24) Vignall, D. A. A. *J. Immunol. Methods* 2000, 243, 243.
25) Egner, B. J.; Rana, S.; Smith, H.; Bouloc, N.; Frey, J. C.; Brocklesby, W. S.; Bradley, M. *Chem. Commun.* 1997, 8, 735.
26) Nolan, J. P.; Sklar, L. A. *Trends Biotechnol,* 2002, 20, 9.
27) Camilla, C.; Mely, L.; Magnan, A.; Casano, B.; Prato, S.; Debono, S.; Montero, F.; Defoort, J. P.; Martin, M.; Fert, V. *Clin. Diagn. Lab. Journal,* 2001, 8, 776.
28) Schrum, D. P.; Culbertson, C. T.; Jacobson, S. C.; Ramsey, J. M. *Anal. Chem.* 1999, 71, 4173.
29) Shapiro, H. *Practical Flow Cytometry,* $3^{rd}$ ed.; Wiley-Liss Inc.; New York, 1995.
30) Lerchi, M.; Bakker, E.; Rusterholz, B.; Simon, W. *Anal. Chem.* 1992, 64, 1534.
31) Lerchi, M.; Reitter, E.; Simon, W.; Pretsch, E.; Chowdhury, D. A.; Kamata, S. *Anal. Chem.* 1994, 66, 1713.
32) Lerchi, M.; Reitter, E.; Simon, W. Fres. *J. Anal. Chem.* 1994, 348, 272.
33) Hisamoto, H.; Nakagawa, E.; Nagatsuka, K.; Abe, Y.; Sato, S.; Siswanta. D.; Suzuki, K. *Anal. Chem.* 1995, 67, 1315.
34) Amiet, G. R.; Farrell, J. R.; Iles, P. J.; Sands, T. J. *Austral. J. Chem.* 2001, 54, 27.
35) Sokalski, T.; Ceresa, A.; Pretsch, E. *J. Am. Chem. Soc.* 1997, 119, 11347.
36) Ceresa, A.; Bakker, E.; Hattendorf, B.; Gunther, D.; Pretsch, E. *Anal. Chem.* 2001, 73, 343.
37) Antico, E.; Lerchi, M.; Rusterholz, B.; Achermann, N.; Badertscher, M.; Valiente, M.; Pretsch, E. *Anal. Chin. Acta* 1999, 388, 327.
38) Fulwyler, M. J.; Perrings, J. D.; Cram, L. S. *Rev. Sclent. Instr.* 1973,44, 204.
39) Bakker, E.; Lerchi, M.; Rosatzin, T.; Rusterholz, B.; Simon, W. *Anal. Chim. Acta* 1993, 278, 211.
40) Telting-Diaz, M.; Bakker, E. *Anal. Chem.* 2001, 73, 5582.
41) Bakker, E.; Simon, W. *Anal. Chem.* 1992, 64, 1805.
42) Bakker, E.; Willer, M.; Pretsch, E. *Anal. Chim. Acta* 1993, 282, 265.

What is claimed is:

1. A method of detecting target ions in a sample, comprising:
    (a) providing ion-detecting polymeric microspheres, said microspheres comprising an ionophore selective for said target ions, and a fluorescent chromoionophore, wherein said polymeric microspheres comprise a copolymer having a glass transitional temperature ($T_g$) of about or below 0° C., wherein said copolymer comprises polymerized units of methacrylate monomers, wherein said methacrylate monomers comprise a monomer having an $R_1$ pendant alkyl group and a monomer having an $R_2$ pendant alkyl group, wherein $R_1$ is any of $C_{1-3}$ alkyl groups and $R_2$ is any of $C_{4-12}$ alkyl groups;
    (b) contacting said microspheres with a flowing stream of said sample under conditions that allow the ion-selective ionophores to bind and form complexes with the ions, if present in the sample, and to cause deprotonation of the chromoionophore, wherein the ionophore/ion complex causes deprotonation of the chromoionophore, and the target ions are extracted into the bulk of the microsphere where they are complexed by the ion-selective ionophores;
    (c) exposing the deprotonated chromoionophore, if formed, to an excitation wavelength light source suitable for exciting the deprotonated chromoionophore of the complexes to emit a fluorescence signal pattern; and
    (d) detecting the fluorescence signal pattern emitted by the complexes, if present, by a detection means for detecting the fluorescence signal pattern, wherein said fluorescence signal pattern is inversely proportional to the amount of said target ions in said sample.

2. The method of claim 1, wherein prior to said contacting step, said microspheres are immobilized on a substrate.

3. The method of claim 1, wherein said sample contains two or more different ions, and said microspheres comprise an ionophore selective for each of said different ions.

4. The method of claim 1, wherein said ionophore is selective for ions selected from the group consisting of sodium ions, potassium ions, and lead ions.

5. The method of claim 1, wherein said chromoionophore is selected from the group consisting of a pH indicating chromoionophore, a pH indicator, and a pH indicating fluoroionophore.

6. The method of claim 1, wherein said microspheres are prepared by a method selected from the group consisting of sonic stream particle casting, solvent casting, and heterogeneous polymerization.

7. The method of claim 1, wherein said microspheres further comprise an ion exchanger.

8. The method of claim 7, wherein the ion exchanger is a salt of a halogenated carborane anion.

9. The method of claim 1, wherein said sample is an environmental sample.

10. The method of claim 1, wherein said sample is a body fluid selected from the group consisting of whole blood, spinal fluid, blood serum, urine, saliva, semen, and tears.

11. The method of claim 1, wherein said complex formation is complete in about 3 to 15 minutes.

12. The method of claim 1, wherein said measurement is obtained by fluorescence microsopy or imaging spectroscopy.

13. The method of claim 1, wherein the size of said sample is about one milliliter.

14. The method of claim 13, wherein said chromoionophore is 11-[(butylpentyl)oxy]-11-oxoundecyl-4-[9-(dimethylamino)5H-benzi[a]phenoxazin-5-yl-indene]aminobenzoate (ETH 5418).

15. The method of claim 14, further comprising 1,1"-dioctadecyl-3,3,3',3'-tetramethylindocarbocyanine perchlorate ($DiIC_{18}$).

16. The method of claim 1, wherein said ionophore is N,N,N',N'-tetradodecyl-3,6-dioxaoctane-1-thio-8-oxodiamide (ETH 5493).

17. The method of claim 16, wherein said method is capable of measuring nanomolar or sub-nanomolar levels of lead ions in said sample.

18. The method of claim 1, wherein said ionophore is tert-butylcalix[4]arene tetraethyl ester (sodium ionophore X).

19. The method of claim 18, wherein said chromoionophore is 9-(diethylamino)-5-octadecanoylimino-5H-benzo[a]phenoxazine (ETH 5294).

20. The method of claim 1, wherein said microspheres further comprise a reference dye.

21. The method of claim 20, wherein said reference dye is 2-[2-[2-chloro-3-[(1,3-dihydro-3,3-dimethyl-1-decylbenzoindol-2-ylidene)ethylidine]-1-cyclohexn-1-yl[ethenyl]-3,3-dimethyl-1-decylbenzoindoliumn iodide or 1,1"-dioctadecyl-3,3',3'-tetramethylindocarbocyanine perchlorate ($DiIC_{18}$).

22. A method of detecting nanomolar or sub-nanomolar levels of lead ions in a sample, comprising;
   (a) providing ion-detecting polymeric microspheres comprising an ionophore selective for said lead ions, a reference dye, a chromoionophore selective for hydrogen ions, and a fluorescent dye, wherein said chromoionophore is a chromoionophore that becomes deprotonated when said lead ions are present in said sample, and wherein said deprotonated form of said chromoionophore is absorbent at the frequency of the fluorescence emission of said dye, wherein said polymeric microspheres comprise a copolymer having a glass transitional temperature ($T_g$) of about or below 0° C., wherein said copolymer comprises polymerized units of methacrylate monomers, wherein said methacrylate monomers comprise a monomer having an $R_1$ pendant alkyl group and a monomer having an $R_2$ pendant alkyl group, wherein $R_1$ is any of $C_{1-3}$ alkyl groups and $R_2$ is any of $C_{4-12}$ alkyl groups;
   (b) contacting said microspheres with a flowing stream of said sample under conditions that allow the ion-selective ionophores to bind and form complexes with the lead ions, if present in the sample, and to cause deprotonation of the chromoionophore, wherein the ionophore/ion complex causes deprotonation of the chromoionophore, and the lead ions are extracted into the bulk of the microsphere where they are complexed by the ion-selective ionophores;
   (c) exposing the dye in microspheres containing said complexes, if formed, to an excitation wavelength light source suitable for exciting the dye to emit a fluorescence signal pattern; and
   (d) detecting the fluorescence signal pattern emitted by the dye by a detection means for detecting the fluorescence signal pattern, wherein said fluorescence signal pattern is inversely proportional to the amount of said lead ions in said sample.

23. The method of claim 22, wherein said ionophore is N,N,N',N'-tetradodecyl-3,6-dioxaoctane-1-thio-8-oxodiamide (ETH 5493).

24. The method of claim 23, wherein said chromoionophore is 11-[(butylpentyl)oxy]-11-oxoundecyl-4-[9-(dimethylamino)$_5$H-benzi[a]phenoxazin-5-yl-indene]aminobenzoate (ETH 5418) and said dye is 1,1"-dioctadecyl-3,3,3',3'-tetramethylindocarbocyanine perchlorate ($DiIC_{18}$).

* * * * *